United States Patent [19]
Hendrickson et al.

[11] Patent Number: 5,740,800
[45] Date of Patent: Apr. 21, 1998

[54] METHOD AND APPARATUS FOR CLINICAL PATHWAY ORDER SELECTION IN A MEDICAL INFORMATION SYSTEM

[75] Inventors: Maria F. Hendrickson, Chelmsford; Michael M. Stern, Needham, both of Mass.

[73] Assignee: Hewlett-Packard Company, Palo Alto, Calif.

[21] Appl. No.: 609,185

[22] Filed: Mar. 1, 1996

[51] Int. Cl.$^6$ ..................................................... A61B 5/00
[52] U.S. Cl. ........................................... 128/630; 128/920
[58] Field of Search ........................ 128/630, 920; 364/413.01, 413.02; 395/200, 202

[56] References Cited

U.S. PATENT DOCUMENTS

| | | | |
|---|---|---|---|
| 5,072,383 | 12/1991 | Brimm et al. | 364/413.01 |
| 5,077,666 | 12/1991 | Brimm et al. | 364/413.02 |
| 5,265,010 | 11/1993 | Evans-Poganelli et al. | 364/413.01 X |
| 5,325,293 | 6/1994 | Dorne | 364/413.01 |
| 5,361,202 | 11/1994 | Dow | 364/413.01 |
| 5,583,758 | 12/1996 | McIlroy et al. | 395/202 |

FOREIGN PATENT DOCUMENTS

WO 94/00817   6/1994   WIPO ........................... G06F 15/00

OTHER PUBLICATIONS

Nursing Workload Management For A patient Data Management System, by K. Roger, et al.; pp. 216–223; 1992.
The Role Of Intelligent Planning And Scheduling In The Diagnostic Process by L. Tandy Herren, et al.; pp. 640–641; 1993.
Care Plan Builder by Kenneth G. Bobis, et al.; pp. 1069–1074; 1992.
Knowledge Representation And Compilation For Symptom– Disease–Test Relationships, by Masahiko Okada, et al.; pp. 547–551; 1989.
Coordinating Advice And Actual Treatment by Thomas A. Russ; pp. 262–262; 1991.
Graphical Representation Of Medical Information In The Visual Chart by Harold Litt, et al.; pp. 252–257; 1994.

*Primary Examiner*—Francis Jaworski

[57] ABSTRACT

A medical information system manages clinical pathway order selection. The medical information system includes a medical database and a user terminal having a display screen. Clinical pathways are defined in the medical database. Each of the clinical pathways is associated with a patient condition and includes a sequence of time intervals and a plurality of clinical pathway order sets. Each of the clinical pathway order sets is associated with a selected one of the time intervals. A selected clinical pathway is associated with a patient in accordance with the patient's condition. When a user selects the patient's clinical pathway order sets, a next order set, which is the first unused order set in the patient's clinical pathway order sets, is determined. A list of the clinical pathway order sets associated with the selected clinical pathway may be displayed on the display screen. The next order set is identified on the list. Clinical pathway order sets that have previously been used for the patient may also be indicated on the list of clinical pathway order sets.

19 Claims, 5 Drawing Sheets

Fig. 1

| Physician Orders | 40 | ICU-North 301 B-1 Frank Jones 14-4 teen 70.0kg | 42 | ? |
|---|---|---|---|---|
| Main Menu | Action | View | Print | Suspend | Store | | Help |

Prompt Region
Allergies: Sulfa

Indications | Order Set Title | Post-op orders | 50

| Entry Data 52 | Action | List of Recent & Pending, Alphabetical | Go To | Details |
|---|---|---|---|---|
| | | Laboratory Tests | 54 | |
| 02/11/95 08:00 | | Chem CS in am | | S * & Ack |
| | | Medications | | |
| 02/11/95 08:01 | | ASA 650 mg po q4h prn for fever above 102 | | * |
| 02/10/95 10:00 | | K Dru 40 meq po qd | | * & Ack |
| 02/11/95 08:02 | Resume | Digoxin in am | | * |
| | | Intravenous Therapy | | |
| 02/10/95 10:02 | | NS at 75 cc/hr | | Ack |

← 56 →

Pathway 66

| Individual | Standard | | |
|---|---|---|---|
| 62 | 64 | | |

Cardiovascular | Non Complicated MI |
Orthopedic | CABG |
Pulmonary | CHF |
Pediatrics | |
Hematology | |
Neurology | |

← 76 → ← 76 →

70 72

*Day 1
*Day 2 80
*Day 3
Variance Day 84

82

← 76 →
74

Close 110

Feb 12 95 1200

METHOD AND APPARATUS FOR CLINICAL PATHWAY ORDER SELECTION IN A MEDICAL INFORMATION SYSTEM

FIELD OF THE INVENTION

This invention relates to computerized medical information systems and, more particularly, to methods and apparatus for managing order selection in a hospital which utilizes clinical pathway models of patient care.

BACKGROUND OF THE INVENTION

The clinical pathway is an approach to patient care within the case management practice model. The clinical pathway represents the events and problems that are expected to occur for a patient with a particular disorder or disease. These events and problems are typically organized on a spreadsheet with time as the horizontal axis. The clinical pathway contains two components: the problem index and the critical path. The problem index includes the problems and outcomes. The critical path includes events that should occur. These events are sorted by category. Clinical pathways may be developed for a variety of different disorders.

The clinical pathway has a number of benefits for a hospital. It establishes a standard of care for specified disorders. Deviations from the clinical pathway can be studied so as to modify and improve care for each disorder. By standardizing care in accordance with the clinical pathways, the hospital can control costs.

The clinical pathway indicates what is expected to happen to the patient for each day or other time period. Many of the events require a written physician order before they can carried out by other health professionals. During the order entry process, the physician must make sure that he writes orders for those events that should occur. If he does not, then the patient's stay in the hospital could potentially be extended, resulting in extra hospital costs. Many hospitals have prepared pre-printed standard order sheets containing the necessary orders for each day on each clinical pathway to assist in this process.

Writing orders corresponding to a clinical pathway is a time consuming task for the physician. The steps performed by the physician in the present manual system are as follows. The physician determines whether the patient is on a clinical pathway. Not all patients are put on a clinical pathway. To determine this, the physician looks in the patient's chart for a pathway. If he is familiar with the patient, he may know already. The physician must determine whether standard order sheets exist for this pathway. If this is a pathway the physician is familiar with, then he may already know. Otherwise, the physician may need to ask a secretary or nurse. The physician needs to associate the patient with a day on the clinical pathway in order to determine what standard order sheets to use. In addition, the physician must determine if the patient is deviating from the clinical pathway. If the patient is not following the expected path, then his plan of care must be individualized to help the patient return to the expected course. The physician must determine whether the patient has other problems that require orders. In some cases, the physician needs to use standard order sheets from another pathway because the patient has multiple problems. The physician must determine what standard order sheets have already been used. To determine this, the physician looks in another part of the patient's chart for the signed order sheets. In some situations, the physician may need to fill out more than one standard order sheet. Finally, the physician must find the appropriate standard order sheets and must complete and sign the order sheets. The manual process can be cumbersome and time consuming.

Computerized medical information systems are widely used to monitor, control and record many aspects of patient care. Clinical pathways have been computerized to some extent. However, the physician order aspect of clinical pathways has not been computerized.

SUMMARY OF THE INVENTION

According to the present invention, methods and apparatus for clinical pathway order selection in a computer-based medical information system are provided. The medical information system includes a medical database and a user terminal having a display screen. Clinical pathways are defined in the medical database. Each of the clinical pathways is associated with a patient condition and includes a sequence of time intervals and a plurality of clinical pathway order sets. Each clinical pathway order set is associated with one of the time intervals. A selected clinical pathway is associated with a patient in accordance with the patient's condition. When a user selects the patient's clinical pathway order sets, a next order set comprising the first unused order set in the patient's clinical pathway order sets is determined. An identification of the next order set is displayed on the display screen.

In a preferred embodiment, a list of the clinical pathway order sets associated with the selected clinical pathway is displayed on the display screen. The next order set is indicated on the list of clinical pathway order sets. Clinical pathway order sets that have been used for the patient may also be indicated on the list of clinical pathway order sets. The user selects an order set from the list. The selected order set, typically the next order set, is displayed, and the user enters desired orders.

According to another aspect of the invention, a medical information system is provided. The medical information system comprises a central processor, including a medical database, and at least one user terminal for entering data into the medical database. The user terminal includes a display screen. The medical information system further Comprises means for defining clinical pathways in the medical database. Each of the clinical pathways is associated with a patient condition and includes a sequence of time intervals and a plurality of clinical pathway order sets, each associated with a selected one of the time intervals. The medical information system further comprises means for associating a selected one of the clinical pathways with a patient in accordance with a patient's condition, means responsive to user selection of the patient's clinical pathway order sets for determining a next order set comprising the first unused order set in the patient's clinical pathway order sets, and means for displaying on the display screen an identification of the next order set. Preferably, the next order set is identified in a list of the clinical pathway order sets associated with the patient's clinical pathway.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
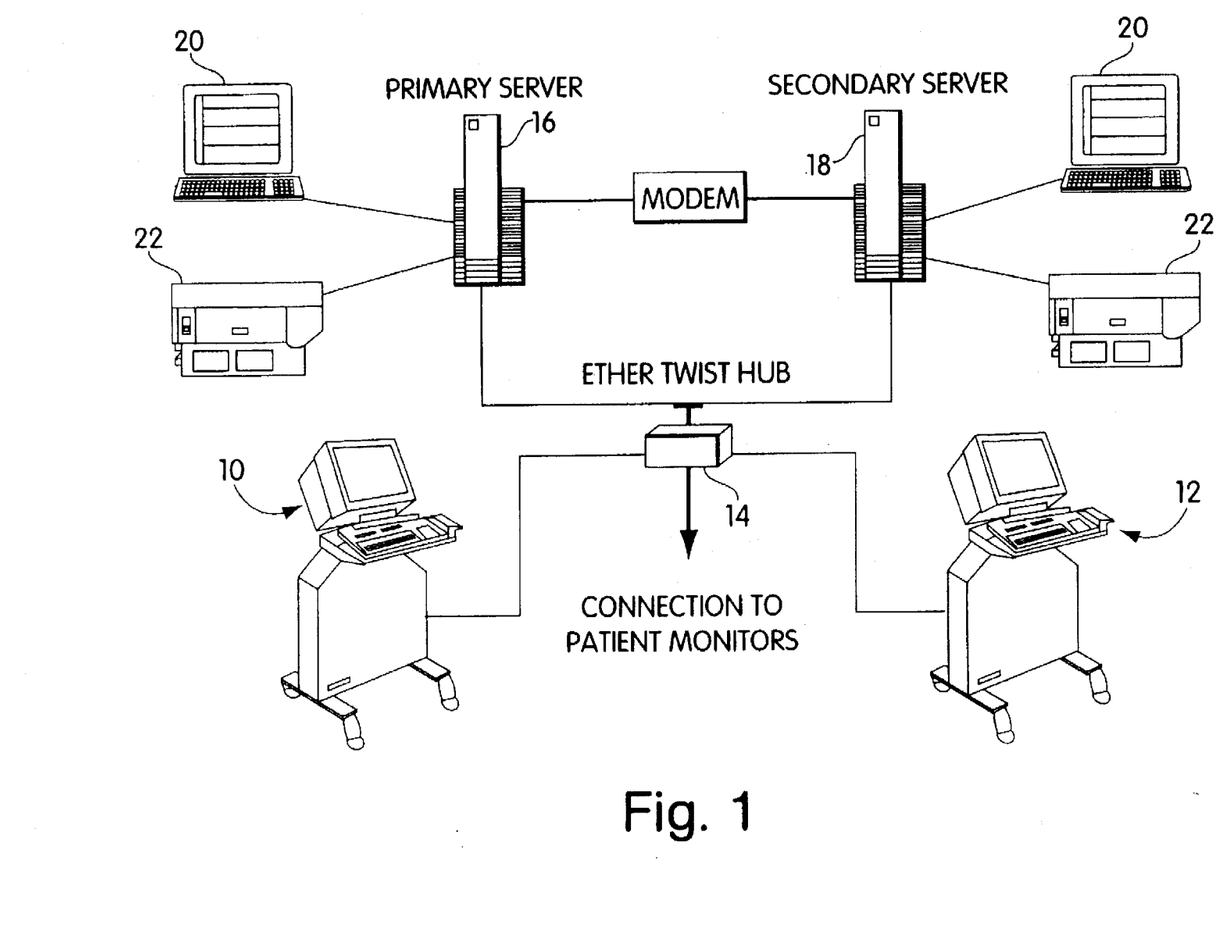
FIG. 1 is a block diagram of an example of a medical information system suitable for practice of the present invention.

The invention is preferably practiced in a computerized medical information system, or clinical information system. The medical information system is designed to provide patient information at the patient's bedside and elsewhere in a hospital. An example of a basic medical information system is shown in FIG. 1. The system uses a client-server architecture wherein a central server supplies data and controls the flow of information to workstations (clients) located at each patient bedside. The client-server architecture eliminates the need for database storage at each workstation.

As shown in FIG. 1, workstations 10 and 12 are connected through a network hub 14 to redundant central servers 16 and 18. Each of the central servers 16 and 18 includes a central processor, memory and disk storage. The servers 16 and 18 perform centralized functions, such as database services, bedside device interface services, hospital system interface services and report services. Each central server typically includes a system manager terminal 20 and a printer 22. Workstations, only two of which are shown in FIG. 1, are typically located at patient bedsides and other locations as required throughout the hospital. Each workstation contains user interface programs and all application programs run by the workstation. The system may also be connected through hub 14 to patient monitors at selected patient bedsides. The patient monitors supply physiological information to the database. An example of a medical information system of the type shown and described is the HP CareVue 9000 system manufactured and sold by the Hewlett-Packard Company.

By way of example, workstations 10 and 12 can be HP 9000 workstations which operate with a diskless processor and include a high resolution graphic display, keyboard and trackball. The workstations typically include 16–32 megabytes of RAM. The central servers 16 and 18 can be implemented as HP 9000 processors coupled to 1.2 gigabytes of disk storage and including 24 megabytes of RAM. The system preferably uses the HP-UX operating system, a robust implementation of the AT&T Unix system V.2. The system also uses the X/Windows graphic user interface. The database is comprised of an HP-Allbase relational database and an object oriented database shell. The system database is shadowed, meaning that it is maintained on both central servers 16 and 18. Both copies of the database are updated with each transaction. Data is initially stored at the workstation and is moved to the server to be stored in the medical database.

Figure 2:
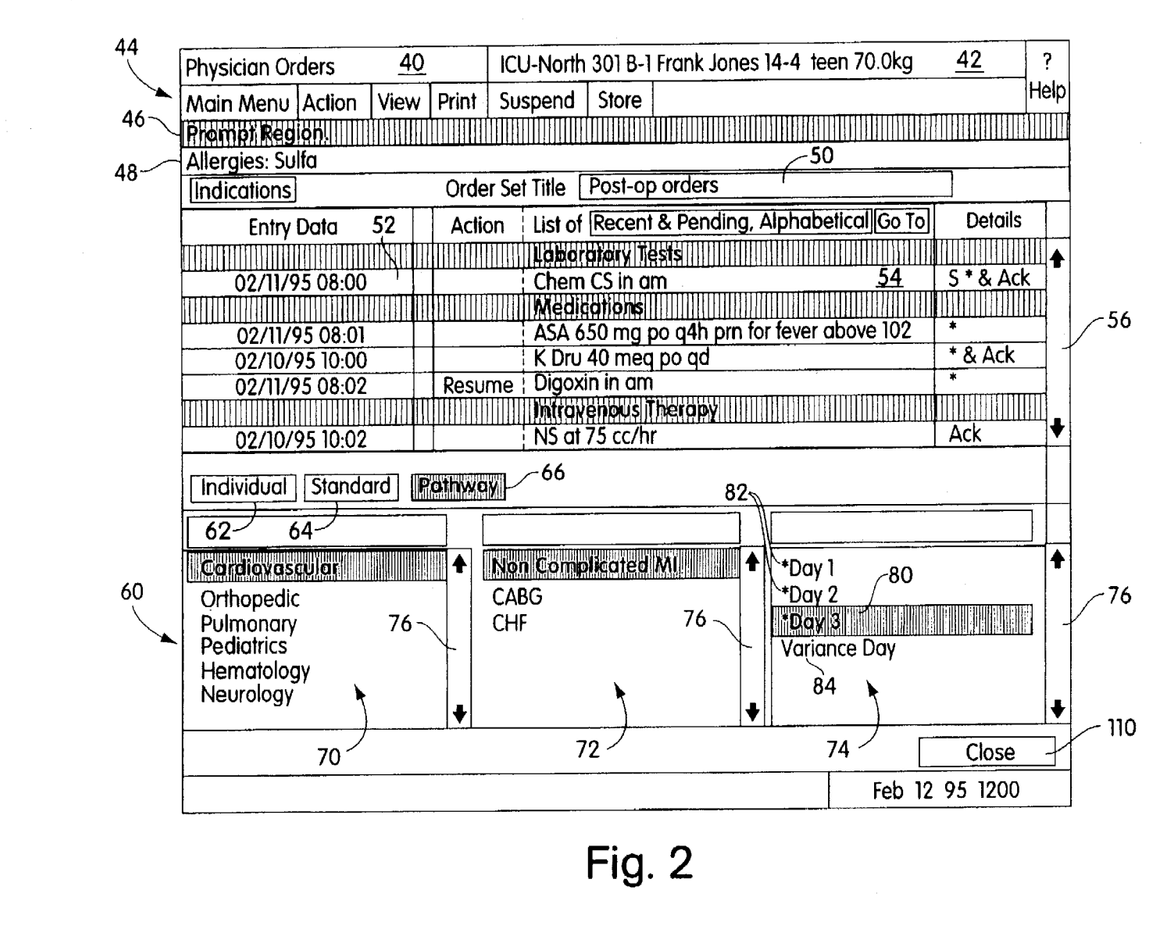
FIG. 2 is an example of a clinical pathway order selection display in the medical information system of FIG. 1.

An example of a physician orders display as it may appear on one of the workstation display screens is shown in FIG. 2. The physician orders display screen provides a concise summary of information relating to physician orders for a selected patient. The physician orders display screen is typically accessed from the main menu of the medical information system. The system utilizes pull down menus having items which may be selected with a pointing device, such as a mouse or trackball, as is conventional in Windows-based systems. In a preferred embodiment, the physician orders display screen is selected from a sub-menu of the patient chart selection on the main menu.

As shown in FIG. 2, the physician orders display screen includes a title area 40, which identifies the display screen, and a patient identification 42. A menu bar 44 may includes a main menu button, an action button, a view button, a print button, suspend button and a store button. As indicated above, selections are made by a pointing device. A prompt region 46 is used to display informational, warning and error type messages to the user. An allergies region 48 indicates any allergies of the patient. When orders have previously been entered for the selected patient, a list of previously entered orders is displayed. The list includes an order set title 50, an order entry date and time 52 and an orders list 54. A scroll bar 56 permits scrolling to additional items on the list.

Below the orders list 54, an order selection list 60 is accessed by a set of order selection buttons, including an individual order sets button 62, a standard order sets button 64 and a clinical pathway order sets button 66. The individual order sets button 62 may be used to access individually defined orders. The standard order sets button 64 may be used to access order sets that are customized for a particular hospital. The clinical pathway order sets button 66 is used to access order sets associated with clinical pathways. In the display screen illustrated in FIG. 2, the clinical pathway order sets button 66 is selected, as indicated by highlighting of that button.

When the clinical pathway order sets button 66 is selected, information regarding the clinical pathway order sets for the selected patient is displayed. A list 70 of clinical pathway categories indicates general categories of clinical pathways. A list 72 of clinical pathways indicates the clinical pathways within a selected category. A list 74 of order sets indicates the order sets, or order sheets, within a selected clinical pathway. Each of the lists 70, 72 and 74 may be provided with a scroll bar 76 to access additional items on the respective lists.

As indicated above, a clinical pathway is a representation of the events that are expected to occur for a patient with a particular disorder. The clinical pathway for a particular disorder is represented by a series of time intervals and the events that are expected to occur during each time interval. The time intervals may be days, several days, hours or any other time intervals that are appropriate for managing the disorder. Different time intervals may be utilized in different portions of the clinical pathway. The clinical pathway is referenced to a starting time which may be the date and time of a patient's surgery or the date and time when the patient was admitted to the hospital with an emergency condition. For example, the clinical pathway may identify events that are expected to occur on day one, day two, day three, etc. following surgery. The clinical pathway may be represented by a spreadsheet with different time intervals indicated horizontally and different events in each time interval listed vertically.

An important aspect of clinical pathways is the clinical pathway order sets associated with each clinical pathway. As indicated above, one or more physician order sets may be associated with some or all of the time intervals in the clinical pathway. Thus, for a clinical pathway representative of a specific disorder, different predefined order sets may be associated with day one, day two, day three, etc. or other suitable time intervals, of the clinical pathway.

In order to implement clinical pathway order selection in accordance with the invention, definitions of the clinical pathways are entered into the medical database during configuration of the medical information system. In particular, each clinical pathway is given a name and is assigned to a category. In addition, each clinical pathway is defined in the database as a sequence of time intervals, such as days. A predetermined order set may be associated with each of the time intervals. Each order set includes the physician orders that may be required during that time interval for a patient having the specified disorder. In general, each time interval may have one or more order sets, or may have no order set. The clinical pathways are defined in the medical database generically without reference to a patient or a starting time. This permits each clinical pathway to be used for multiple patients.

When a patient has not been assigned to a clinical pathway and the user selects the clinical pathway order sets button 66, the categories list 70, the clinical pathways list 72 and the order sets list 74 appear on the display screen with default values highlighted. The listed categories, clinical pathways and order sets represent the clinical pathway definitions that were entered into the medical database during configuration of the system.

The patient is associated with a clinical pathway, preferably early in his or her hospital stay. The user, which may be a physician, selects a category of clinical pathway on list 70 and selects a specific clinical pathway from list 72. Alternatively, a selected clinical pathway may be assigned to the patient using a clinical pathway display screen (not shown). The selected clinical pathway is assigned to the patient and remains assigned to the patient during his or her stay in the hospital unless a subsequent change is made. In subsequent accesses to the clinical pathway order sets for the patient, the selected clinical pathway is automatically displayed.

In the example illustrated in FIG. 2, a clinical pathway was previously assigned to the patient. Thus, when the user selected the clinical pathway order sets button 66, the previously selected category and clinical pathway are highlighted on lists 70 and 72, respectively. In addition, a next order set 80 is indicated on list 74, preferably by highlighting. The next order set 80 is the first order set in the list of order sets which has not been used for the patient. Since the next order set is indicated on list 74, the physician or other user is not required to determine which time interval of the clinical pathway the patient is on and is not required to look for an order sheet associated with that time interval. The next order set is indicated, even if the patient is deviating from the schedule defined in the clinical pathway.

The order sets list 74 preferably includes an indication of any order sets that have already been used for the patient. In the example of FIG. 2, the day one and day two order sets are preceded by asterisks 82, which indicate that these order sets have been used for the patient. Thus, the user can easily observe the next order set 80 and those order sets that have been used for the patient. It will be understood that any suitable indicators may be used to identify the next order set and previously used order sets. Under normal circumstances, the user selects the next order set. However, the system does not place restrictions on which order sets may be selected. For example, the physician may realize that the patient is deviating from the clinical pathway and may select another order set from list 74, including order sets that have already been used. If the patient goes off the clinical pathway, the user may select a variance day order set 84. The variance day order set 84 is an order set that is specifically designed for the case where the patient goes off, or deviates from, the clinical pathway.

Figure 3:
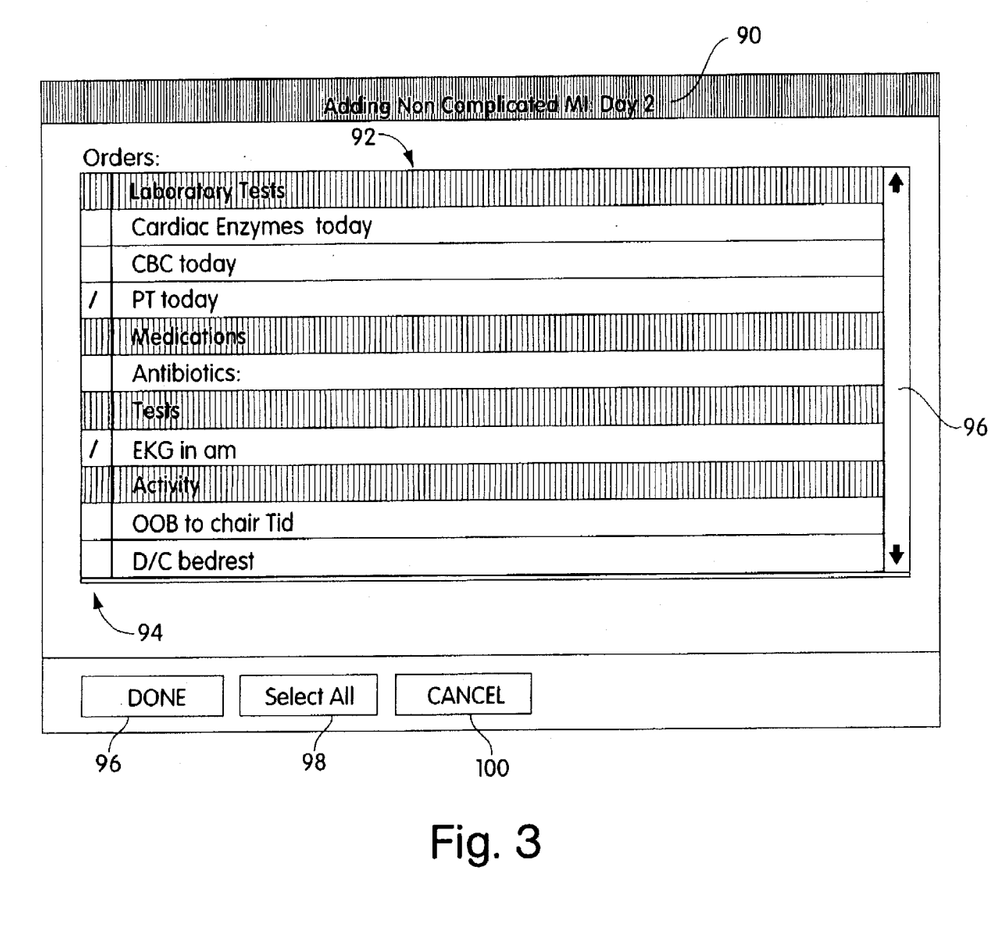
FIG. 3 is an example of a clinical pathway order set used in the medical information system of FIG. 1.

When the user selects an order set from list 74, a clinical pathway order set dialog box is displayed on the display screen. An example of a clinical pathway order set dialog box is shown in FIG. 3. The dialog box overlays the display screen shown in FIG. 2. The order set dialog box contains a list of orders that may be appropriate for the particular time interval in the clinical pathway. The dialog box includes a title 90 which identifies the clinical pathway and the time interval. The dialog box also includes a list 92 of specific orders. A character in a column 94 preceding the orders indicates which orders have been selected by the user. Orders are selected using the pointing device. A scroll bar 96 may be used to access additional orders in the order set. The dialog box also includes control buttons, including a done button 96 to indicate completion of the order set, a select all button 98 and a cancel button 100. Following completion of the order set, the dialog box is removed from the display screen, and the orders are processed as required. For example, orders requiring specific actions are sent to appropriate departments in the hospital. In addition, the orders are recorded in the medical database as a part of a recordkeeping function. At this time, the user may select another order set from the clinical pathway order sets or from the individual or standard order sets. Alternatively, the user may close the physician order function by selecting the close button 110 on the display shown in FIG. 2.

Figure 4A:
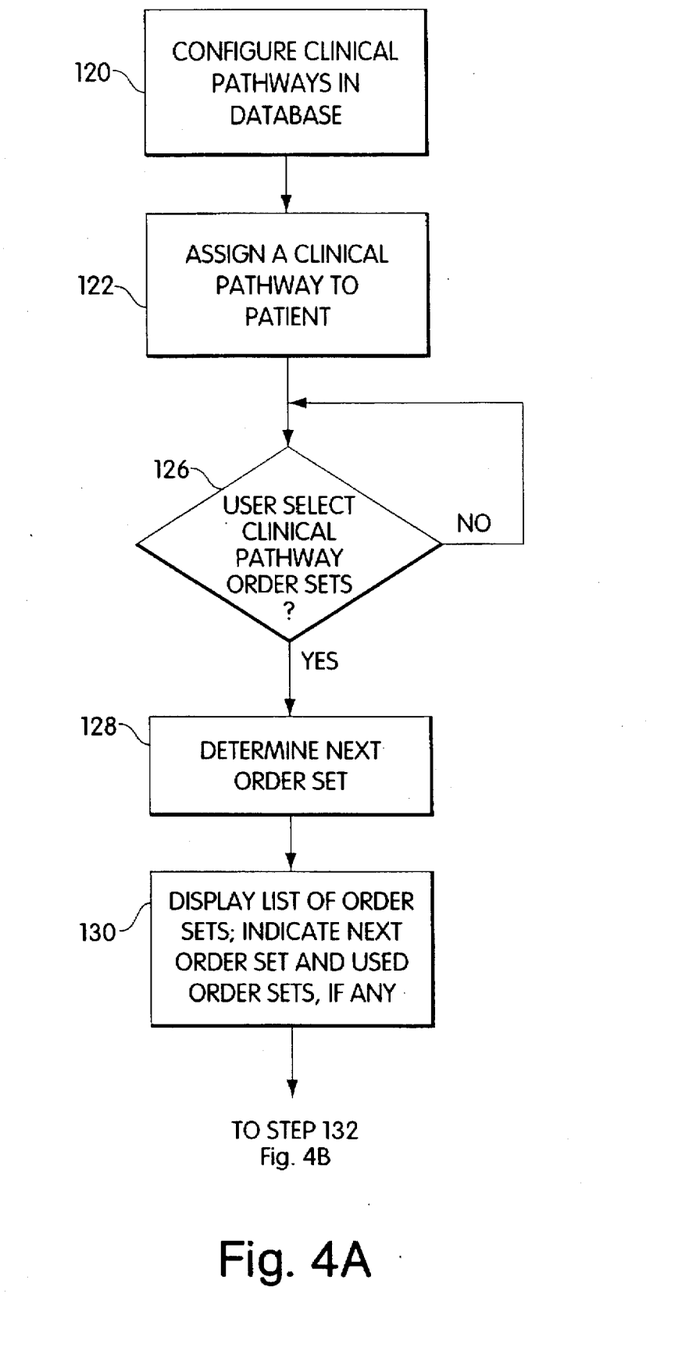
FIGS. 4A and 4B show a flow diagram of an example of the physician order selection process in accordance with the invention.
Figure 4B:
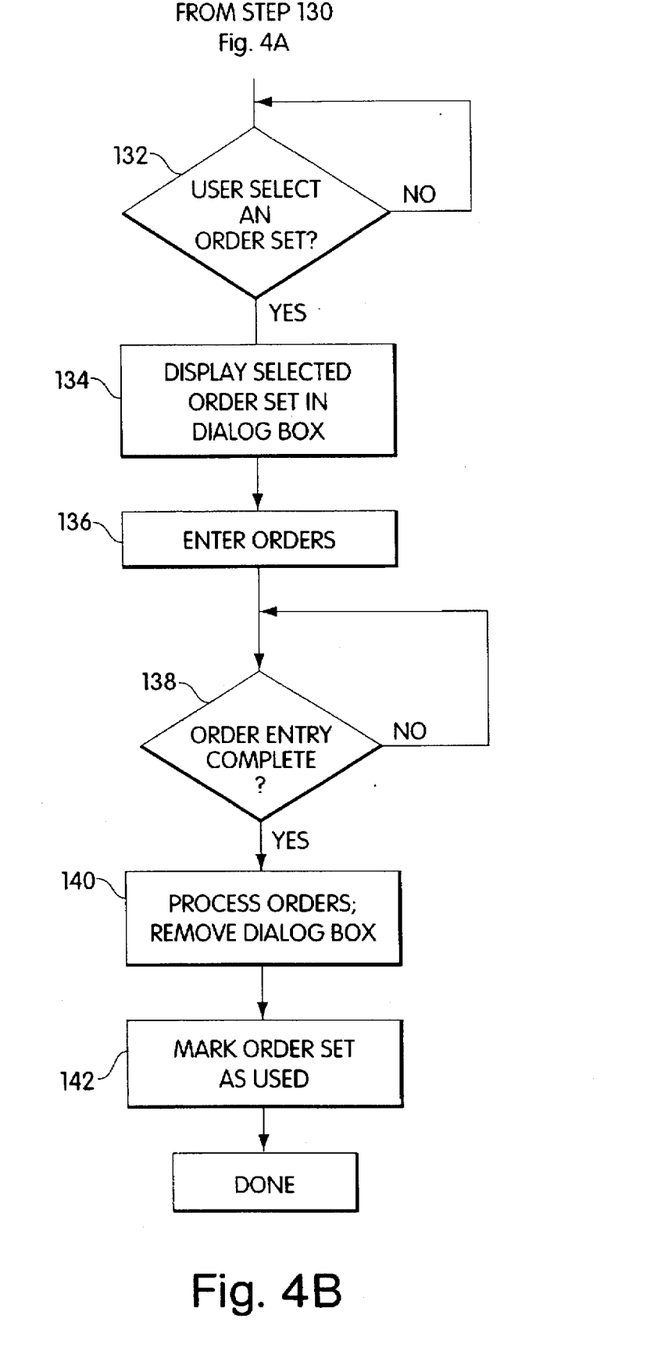

Operation of the clinical pathway order selection function in accordance with the present invention is illustrated in the flow chart of FIGS. 4A and 4B. Initially, the clinical pathways are configured in the medical database in step 120. As indicated above, each clinical pathway includes a name, a category, a sequence of time intervals and order sets associated with one or more of the time intervals. A typical clinical pathway may include a sequence of days and an order set for each day in the sequence. The order sets thus form an ordered sequence. The steps required to access the physician orders display screen of FIG. 2 are omitted for ease of understanding. In step 122, a selected clinical pathway is assigned to a patient in accordance with the patient's disorder. A clinical pathway may be assigned to the patient in the physician orders display screen or may be assigned to the patient in a separate clinical pathway display screen. The selected clinical pathway remains assigned to the patient until the clinical pathway is changed or deleted, or the patient is discharged from the hospital. More than one clinical pathway may be assigned to a patient, depending on the patient's condition. A clinical pathway is assigned to the patient by selecting a category from list 70 and a clinical pathway from list 72.

When the user selects clinical pathway order sets in step 126, (by selecting the clinical pathway order sets button 66 in FIG. 2), the next order set is determined in step 128. The next order set is the first order set in the ordered sequence of order sets that has not been used for the patient. In step 130, a list of order sets for the selected clinical pathway is displayed. The next order set and used order sets, if any, are indicated. The list of clinical pathway order sets corresponds to the list 74 shown in FIG. 2 and described above. The next order set may, for example, be indicated by highlighting, and used order sets may be indicated by asterisks. The list 70 of clinical pathway categories and the list 72 of clinical pathways are not used after a clinical pathway has been assigned to the patient in step 122.

When the user selects an order set in step 132, (by selecting one of the order sets from list 74 in FIG. 2), the selected order set is displayed as a dialog box in step 134. The dialog box corresponds to the clinical pathway order set dialog box shown in FIG. 3 and described above. In step 136, the user enters orders in the order set dialog box. When order entry is determined to be complete in step 138, the orders are processed in step 140. As indicated above, processing of orders may involve sending orders to appropriate departments and recording orders in the medical database. In addition, the order set dialog box is removed from the display screen in step 140. In step 142, the order set completed in step 138 is marked as used. When the order set is marked as used, an asterisk or other indication appears before the order set on order sets list 74. When the clinical pathway order sets for the patient are subsequently accessed, the user will immediately recognize that the order set has previously been used for that patient. Following step 142, the clinical pathway order selection and entry process is complete.

In the clinical pathway order selection process described above, the user selects the next order set or an alternative order set from a list of clinical pathway order sets. In an alternative configuration, the medical information system may display the next order set in a clinical pathway order set dialog box upon selection of clinical pathway order set button 66 shown in FIG. 2. This assumes that the user in most cases will wish to select the next order set. In this embodiment, the order set dialog box may include a button for selection of an alternate order set when the next order set is not appropriate.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for clinical pathway order selection in a computer-based medical information system including a medical database and a user terminal having a display screen, said method comprising the steps of:

defining clinical pathways in the medical database, each of said clinical pathways being associated with a patient condition and including a sequence of time intervals and a plurality of clinical pathway order sets, each being associated with a selected one of said time intervals;

associating a selected one of said clinical pathways with a patient in accordance with the patient's condition;

in response to user selection of the patient's clinical pathway order sets, determining a next order set comprising a first unused order set in the patient's clinical pathway order sets; and displaying on the display screen an identification of the next order set.

2. A method for clinical pathway order selection as defined in claim 1, further including the step of displaying on the display screen, in response to user selection of the patient's clinical pathway order sets, a list of the clinical pathway order sets associated with the selected clinical pathway.

3. A method for clinical pathway order selection as defined in claim 2, wherein the step of displaying an identification of the next order set includes indicating the next order set on said list of clinical pathway order sets.

4. A method for clinical pathway order selection as defined in claim 2, further including the step of indicating on the list of clinical pathway order sets those clinical pathway order sets that have previously been used for the patient.

5. A method for clinical pathway order selection as defined in claim 2, further including the steps of displaying the next order set on the display screen in response to user selection of the next order set and processing orders selected by the user from the next order set.

6. A method for clinical pathway order selection as defined in claim 2 wherein the list of clinical pathway order sets includes a variance day order set that is specifically designed for the case where the patient deviates from the selected clinical pathway and further including the step of displaying the variance day order set in response to user selection of the variance day order set.

7. A method for clinical pathway order selection as defined in claim 1, wherein the step of associating a selected one of said clinical pathways with a patient includes associating different ones of said clinical pathways with different patients in accordance with each patient's condition.

8. A method for clinical pathway order selection as defined in claim 1 further including the step of displaying on the display screen, in response to user selection of the patient's clinical pathway order sets, a list of clinical pathway categories, a list of clinical pathways for a selected category and a list of clinical pathway order sets for the selected clinical pathway.

9. A method for clinical pathway order selection as defined in claim 8 further including the step of indicating the next order set on said list of clinical pathway order sets.

10. A method for clinical pathway order selection in a computer-based medical information system including a medical database and a user terminal having a display screen, said method comprising the steps of:

defining clinical pathways in the medical database, each of said clinical pathways being associated with a patient condition and including a sequence of time intervals and a plurality of clinical pathway order sets, each being associated with a selected one of said time intervals;

associating a selected one of said clinical pathways with a patient in accordance with the patient's condition;

in response to user selection at the user terminal of the patient's clinical pathway order sets, displaying on the display screen a list of the patient's clinical pathway order sets;

indicating on the list of clinical pathway order sets a next order set comprising a first unused order set in the patient's clinical pathway order sets;

displaying the next order set on the display screen in response to user selection of the next order set; and processing orders selected by the user from the next order set.

11. A method for clinical pathway order selection as defined in claim 10, further including the step of indicating on the list of clinical pathway order sets those clinical pathway order sets that have previously been used for the patient.

12. A method for clinical pathway order selection as defined in claim 10 further including the step of displaying on the display screen a list of clinical pathway categories and a list of clinical pathways for a selected category in response to user selection of the patient's clinical pathway order sets.

13. A method for clinical pathway order selection as defined in claim 10 wherein the list of clinical pathway order sets includes a variance day order set that is specifically designed for the case where the patient deviates from the selected clinical pathway and further including the step of displaying the variance day order set in response to user selection of the variance day order set.

14. A medical information system comprising:

a central processor, including a medical database, and at least one user terminal for entering data into said medical database, said user terminal including a display screen;

means for defining clinical pathways in the medical database, each of said clinical pathways being associated with a patient condition and including a sequence of time intervals and a plurality of clinical pathway order sets, each being associated with a selected one of said time intervals;

means for associating a selected one of said clinical pathways with a patient in accordance with the patient's condition;

means responsive to user selection of the patient's clinical pathway order sets for determining a next order set comprising a first unused order set in the patient's clinical pathway order sets; and means for displaying on the display screen an identification of the next order set.

15. A medical information system as defined in claim 14 further including means responsive to user selection of the patient's clinical pathway order sets for displaying on the display screen a list of the clinical pathway order sets associated with the selected clinical pathway.

16. A medical information system as defined in claim 15 wherein said means for displaying an identification of the next order set includes means for indicating the next order set on said list of clinical pathway order sets.

17. A medical information system as defined in claim 15 further including means for indicating on the list of clinical pathway order sets those clinical pathway order sets that have previously been used for the patient.

18. A medical information system as defined in claim 15 further including means responsive to user selection of the next order set for displaying the next order set on the display screen and means for processing orders selected by the user from the next order set.

19. A medical information system as defined in claim 14 further including means responsive to user selection of the patient's clinical pathway order sets for displaying on the display screen a list of clinical pathway categories, a list of clinical pathways for a selected category and a list of clinical pathway order sets for the selected clinical pathway.

* * * * *